United States Patent [19]
Iversen

[11] Patent Number: 6,024,702
[45] Date of Patent: Feb. 15, 2000

[54] IMPLANTABLE ELECTRODE MANUFACTURED WITH FLEXIBLE PRINTED CIRCUIT

[75] Inventor: Alfred A. Iversen, Wayzata, Minn.

[73] Assignee: PMT Corporation, Chanhassen, Minn.

[21] Appl. No.: 08/922,935

[22] Filed: Sep. 3, 1997

[51] Int. Cl.$^7$ ........................................ A61B 5/04
[52] U.S. Cl. ............................................ 600/378
[58] Field of Search ................... 600/373, 377, 600/378, 329, 483

[56] References Cited

U.S. PATENT DOCUMENTS

| | | |
|---|---|---|
| 3,572,322 | 3/1971 | Wade ..................................... 600/483 |
| 4,461,304 | 7/1984 | Kuperstein . |
| 4,735,208 | 4/1988 | Wyler et al. . |
| 4,785,672 | 11/1988 | Picone . |
| 4,869,255 | 9/1989 | Putz . |
| 5,493,074 | 2/1996 | Murata et al. . |
| 5,569,886 | 10/1996 | Tanabe et al. . |

OTHER PUBLICATIONS

Sonn et al, "Medical + Biological Engineering" pp. 778–790, Nov. 1974.
Schaudinischky et al, Medical + Biological Engineering, vol. 7, pp 341–343 + picture, 1969.

*Primary Examiner*—William E. Kamm
*Attorney, Agent, or Firm*—Anthony G. Eggink

[57] ABSTRACT

An implantable electrode for monitoring tissue electrical activity and for tissue electrical stimulation comprises a flexible electrode body for contacting human body tissue, a connector portion having a plurality of connectors for connection to external monitoring equipment, the connector portion connected to the electrode body, both the electrode body and the connector portion being comprised of a thin, flexible, non-conducting backing material, a printed circuit etched onto the flexible backing material, the printed circuit further comprising a plurality of electrical contact areas of a conductive material for contacting the tissue, and a plurality of electrical leads connecting the electrical contact areas to the connectors, and a flexible, non-conducting covering material covering the printed circuit, the electrical contact areas extending through the covering material. A method of manufacture of the electrode is also disclosed.

21 Claims, 3 Drawing Sheets

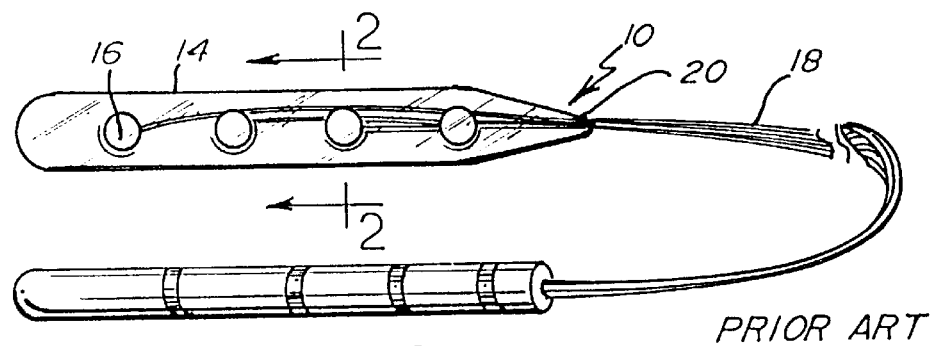
Fig. 1.
PRIOR ART
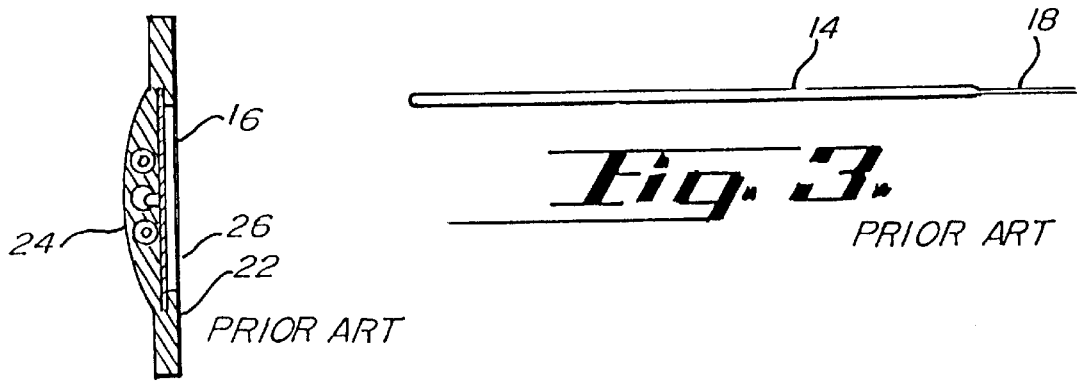
Fig. 2.
PRIOR ART
Fig. 3.
PRIOR ART
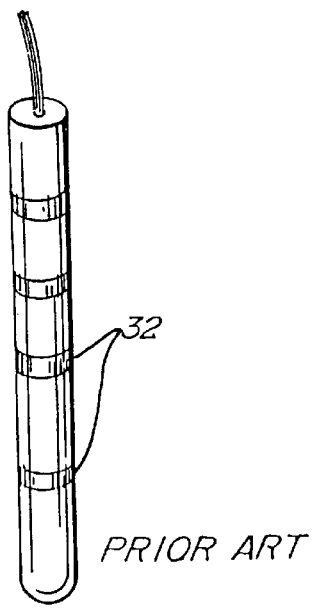
Fig. 4.
PRIOR ART

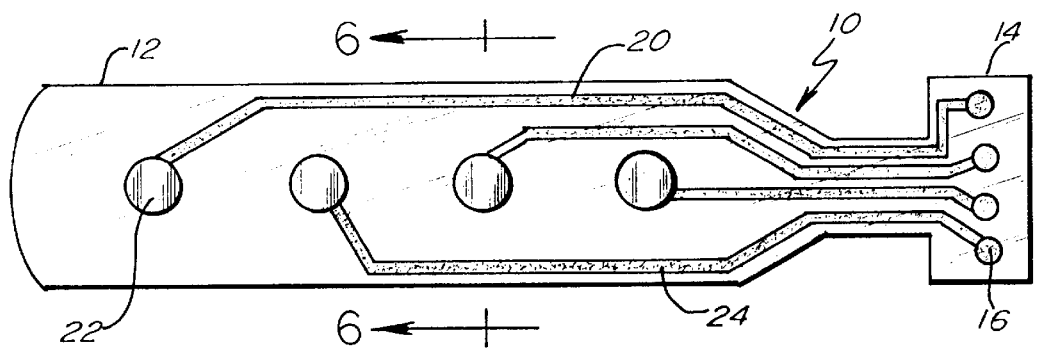
Fig. 5.
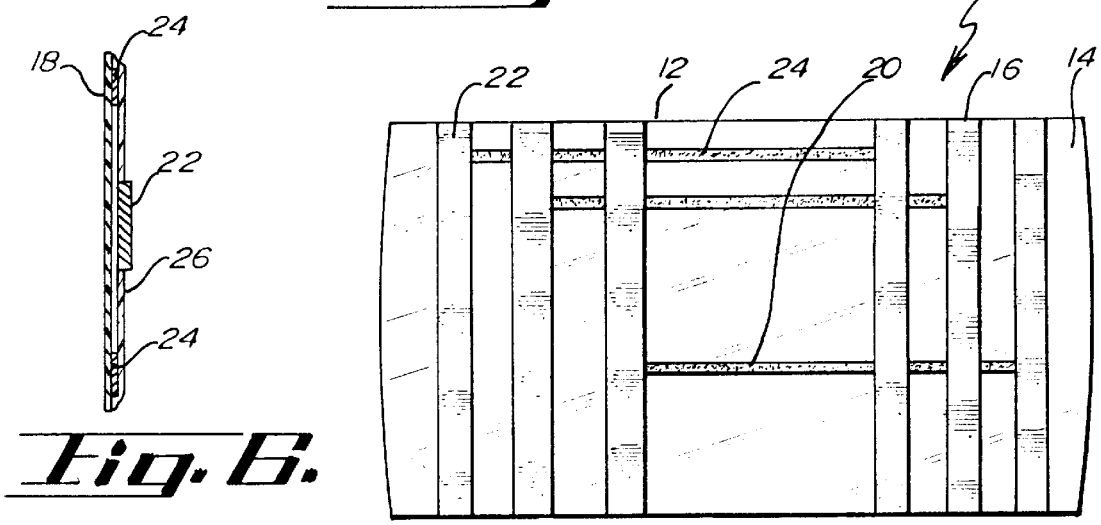
Fig. 6.
Fig. 7.
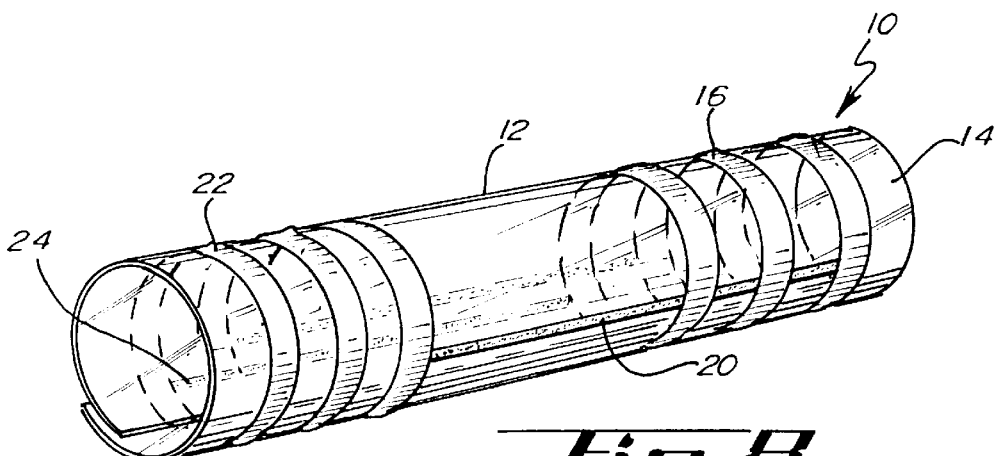
Fig. 8.

IMPLANTABLE ELECTRODE MANUFACTURED WITH FLEXIBLE PRINTED CIRCUIT

BACKGROUND OF THE INVENTION

This invention is related generally to electrodes for monitoring cortical electrical activity in order to define epileptogenic foci. However, the invention is not limited to monitoring brain electrical activity but also has improved features for monitoring and electrical stimulation of brain and other tissue.

Surgical removal of epileptogenic brain is indicated for treatment of many medically refractory focal seizure disorders. One of the important factors in providing good results from such surgery is the degree of accuracy in identifying epileptogenic foci. Various methods have been used in attempting to determine epileptogenic foci, and all involve sensing of cortical electrical activity using electrical contacts applied in various ways.

Standard scalp contacts have been used for many years, but accurate localization is usually very difficult with recordings obtained from such contacts. Therefore, many epilepsy centers in recent years have used intracranial recording techniques to better define regions of cortical epileptogenicity.

Intracranial recording techniques have used either of two different types of electrodes—intracortical depth electrodes or subdural strip electrodes. The far more commonly used technique of intracranial recording uses intracortical depth electrodes, but other techniques using subdural strip electrodes, first utilized many years ago, have been shown to be relatively safe and valuable alternatives.

The relative safety of subdural strip electrodes lies in the fact that, unlike depth electrodes, they are not invasive of brain tissue. Depth electrodes are narrow, typically cylindrical dielectric structures with contact bands spaced along their lengths. Such electrodes are inserted into the brain in order to establish good electrical contact with different portions of the brain. These electrodes must be stiff in order to penetrate brain tissue. Subdural strip electrodes, on the other hand, are generally flat strips supporting contacts spaced along their lengths. Such strip electrodes are inserted between the dura and the brain, along the surface of and in contact with the brain, but not within the brain.

A typical subdural strip electrode of the prior art is shown in FIGS. 1–4 and is disclosed in U.S. Pat. No. 4,735,208. The '208 patent discloses a subdural strip electrode 10 having an elongated flexible silicone dielectric strip 14, a plurality of spaced aligned flat electrical stainless steel contact disks 16 held within dielectric strip 14, and lead wires 18 exiting strip 14 from a proximal end 20 thereof.

Dielectric strip 14 of strip electrode 10 has front and back dielectric layers 22 and 24, respectively. Each front layer 22 has a front layer opening 26 for each contact disk 16. Openings 26 are circular and somewhat smaller in diameter than contact disks 16. Front and back layers 22 and 24 are sealed together by adhesive and/or heat such that they form, in essence, an integral dielectric strip.

The dielectric strips are generally made of a flexible, non-conductive material in order to allow the subdural strip electrode to conform to the surface of the brain. For this reason, metals are generally inappropriate for the dielectric strip.

The subdural strip electrodes of the prior art are predominately rectangular in cross-section. Other subdural strip electrodes of the prior art have a circular or round cross section.

The lead wires are generally routed out through a stab wound in the skin remote from the electrode and generally terminate in a distal end with ring-type terminals. These ring-type terminals are then connected to monitoring equipment by means of a connector. Such a prior connector is disclosed in U.S. Pat. No. 4,869,255.

The structure of these prior art electrodes results in high manufacturing costs. Generally, the contact disks and lead wires are manually placed onto one of the dielectric strips; the second dielectric strip is placed over the contact disks and lead wires; and the two dielectric strips are sealed together. Because the location of the contact disks within the brain must be precisely known in order to determine epileptogenic foci, the contact disks must be precisely placed along the dielectric strip. The lead wires are thin and may easily tangle with each other or may be twisted or broken during the assembly process. Therefore, careful quality control of the assembly process is necessary.

Additionally, the thin lead wires may have a high electrical resistance, causing problems with recording brain electrical activity.

After lead wires exit the proximal end of the electrode, they are no longer supported by the flexible electrode matrix and may break.

An additional manufacturing step is necessary to manufacture the ring-type terminals.

There is a need for an improved implantable electrode which may be manufactured with a printed circuit to lower manufacturing costs and improve quality control.

Flexible printed circuits have been used for some time in electronic devices such as liquid crystal display tubes, ECD and solar cells for mechanically and electrically connecting electrode portions of the electronic devices and a printed circuit board. Such flexible printed circuits are discussed in U.S. Pat. No. 5,493,074 and U.S. Pat. No. 5,569,886, herein incorporated by reference.

U.S. Pat. No. 4,461,304 discloses a microelectrode for insertion into the brain with parts of the microelectrode formed of a printed circuit. However, this electrode is not suitable for use as a subdural strip electrode because the electrode is not flexible and the substrate is a metal. Furthermore, the problem addressed by the '304 patent is different from the problem being addressed in this application. The '304 patent addresses the problem of recording the electrical potentials of individual neurons of the brain. The current patent application addresses the problem of recording brain electrical activity at a much grosser level, that is, at epileptogenic foci, which may comprise thousands or tens of thousands of neurons.

SUMMARY OF THE INVENTION

An implantable electrode for monitoring tissue electrical activity and for tissue electrical stimulation comprises a flexible electrode body for contacting human body tissue, a connector portion having a plurality of connectors for connection to external monitoring equipment, the connector portion connected to the electrode body, both the electrode body and the connector portion being comprised of a thin, flexible, non-conducting backing material, a printed circuit etched onto the flexible backing material, the printed circuit further comprising a plurality of electrical contact areas of a conductive material for contacting the tissue, and a plurality of electrical leads connecting the electrical contact areas to the connectors, and a flexible, non-conducting covering material covering the printed circuit, the electrical contact areas extending through the covering material. A method of manufacture of the electrode is also disclosed.

A principal object and advantage of the present invention is that it may be manufactured at substantially lower cost than earlier tissue electrodes.

A second object and advantage of the present invention is that the manufacturing process will introduce fewer defects than that used in earlier tissue electrodes.

Another object and advantage of the present invention is that there are no unsupported wires between the electrode body and the connector portion, reducing the likelihood of breakage.

BRIEF DESCRIPTION OF THE DRAWINGS

FIG. 1 is a perspective view of a subdural strip electrode and connector of the prior art.

FIG. 2 is a cross-section along the lines 2 of FIG. 1.

FIG. 3 is a side elevational view of the prior art electrode of FIG. 1.

FIG. 4 is a perspective view of a connector of the prior art.

FIG. 5 is a plan view of the implantable electrode of the present invention.

FIG. 6 is a cross-section along the lines 6 of FIG. 5.

FIG. 7 is a plan view of a second embodiment of the implantable electrode of the present invention.

FIG. 8 is a perspective view of the electrode of FIG. 7, after the electrode has been rolled into a cylinder.

DETAILED DESCRIPTION OF THE PREFERRED EMBODIMENTS

Figure 9:
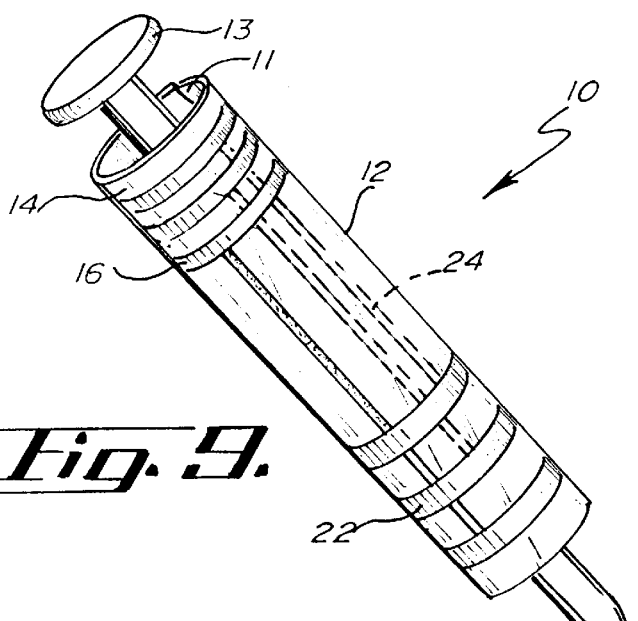
FIG. 9 is a perspective view of the electrode of FIG. 8, showing a removable stylet.

A typical subdural strip electrode of the prior art is shown in FIGS. 1–4 and is disclosed in U.S. Pat. No. 4,735,208. The '208 patent discloses a subdural strip electrode 10 having an elongated flexible silicone dielectric strip 14, a plurality of spaced aligned flat electrical stainless steel contact disks 16 held within the dielectric strip 14 and lead wires 18 exiting the strip 14 from a proximal end 20 thereof.

Dielectric strip 14 of strip electrode 10 has front and back dielectric layers 22 and 24, respectively. Each front layer 22 has a front layer opening 26 for each contact disk 16. Openings 26 are circular and somewhat smaller in diameter than contact disks 16. Front and back layers 22 and 24 are sealed together by adhesive and/or heat such that they form, in essence, an integral dielectric strip.

The implantable electrode of the present invention is shown generally in the Figures as reference numeral 10.

The implantable electrode 10 comprises a flexible electrode body 12 adapted to contact human body tissue. As can be seen in the Figures, the electrode body 12 may be any shape, but is preferably flat and elongate (FIG. 5), cylindrical (FIG. 9), or substantially rectangular (FIG. 10). The electrodes of FIG. 5 are generally referred to as strip electrodes. The cylindrical electrode 10 in FIG. 9 further comprises a central axial core 11 and a removable stylet 13 within the axial core adapted to penetrate body tissue. The electrodes of FIG. 10 are generally referred to as grid electrodes.

A connector portion 14 is connected to the electrode body 12. The connector portion 14 has a plurality of connectors 16 for connection to external monitoring equipment (not shown).

Both the electrode body 12 and the connector portion 14 are preferably comprised of a thin, flexible, non-conducting backing material 18.

A printed circuit 20 is etched onto the flexible, non-conducting backing material 18 as is known in the art. One method of etching the printed circuit onto the backing material is disclosed in U.S. Pat. No. 5,493,074, herein incorporated by reference. The flexible, non-conductive backing material may preferably be mylar or silicone.

The printed circuit 20 further comprises a plurality of electrical contact areas 22 of a conductive material for contacting the tissue, and a plurality of electrical leads 24 connecting the electrical contact areas 22 to the connectors 16. The connectors 16 also preferably are part of the printed circuits. Alternatively, the connectors 16 may be attached to the printed circuit 20 by any method, such as soldering. Preferably, the electrical contact areas 22 are comprised of a metal. Most preferably, the metal is selected from the group consisting of stainless steel, platinum, and platinum/iridium. However, any other conducting metal such as gold or copper could also be used. Alternatively, the electrical contact areas could be formed of a non-metallic conducting material such as conformable conductive silicone rubber as disclosed in U.S. Pat. No. 4,461,304.

In the grid electrode of FIG. 10, the electrical contact areas 22 are preferably arranged in a two-dimensional grid.

A flexible, non-conducting covering material 26 covers the printed circuit 20 and prevents contact between the electrical leads 24 and the tissue. The electrical contact areas 22 extend through the covering material 26. The flexible, non-conductive covering material may preferably be mylar or silicone.

Figure 11:
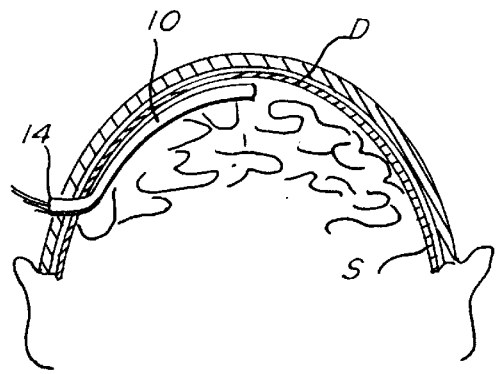
FIG. 11 is a cross-section of the human skull showing the implantable electrode of the present invention inserted between the brain surface and the dura.

The electrodes 10 of the present invention are preferably used as subdural electrodes and are inserted between the brain surface S and the dura D as shown in FIG. 11

Figure 10:
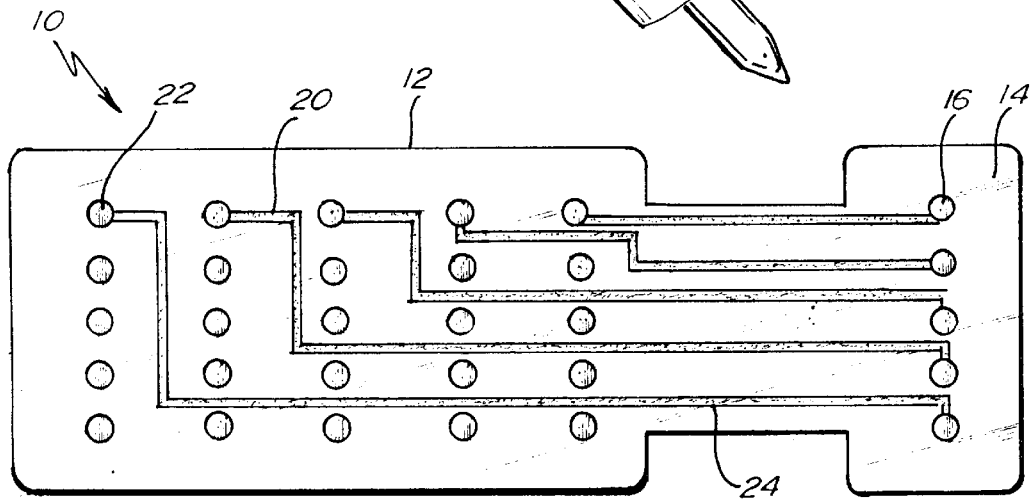
FIG. 10 is a plan view of a third embodiment of the implantable electrode of the present invention. Only part of the printed circuit is illustrated.

Alternatively, the electrode of FIG. 9 with a removable stylet 13 may be used to tunnel through tissue, with the stylet 13 being removed after insertion of the electrode.

The electrodes 10 of the present invention may be manufactured as follows.

First, a flexible, elongated electrode body 12 and a connector portion 14 are produced. Both the electrode body 12 and connector portion 14 are preferably composed of a thin, flexible, non-conducting backing material 18 as already disclosed. The flexible, non-conductive backing material may preferably be mylar or silicone. Preferably, the electrode body 12 and the connector portion 14 are manufactured as a single unit, as by plastic molding techniques.

Next, a printed circuit 20 is etched onto the flexible, non-conducting backing material 18 by techniques known in the art. One method of etching the printed circuit onto the backing material is disclosed in U.S. Pat. No. 5,493,074, herein incorporated by reference. As disclosed above, the printed circuit 20 may comprise a plurality of electrical contact areas 22, a number of connectors 16, and a plurality of electrical leads 24 connecting the electrical contact areas 22 with the connectors 16. Alternatively, the contact areas 22 and/or the connectors 16 may be attached to the electrical leads 24 by any method, such as soldering.

Next, the printed circuit 20 is covered with a flexible, non-conducting covering material 26, allowing the electrical contact areas 22 to extend through the covering material 26. For example, the electrical contact areas may be masked off and the covering material 26 bonded to the backing material 18. Alternatively, openings may be pre-cut in the covering material for the electrical contact areas 22. The covering material may preferably be mylar or silicone.

In a further manufacturing step, the electrode of FIG. 9 may be produced by rolling an elongated electrode body, produced as above, into a cylinder, as shown in FIG. 8, producing a cylindrical electrode with the electrical contact areas and connectors along the periphery of the cylinder. The edges of the cylinder are then sealed to one another. Then a removable stylet 13 may preferably be inserted within the cylinder, producing the electrode shown in FIG. 9.

In a further step (not shown), one end of the cylindrical electrode may be sealed.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. An electrode for implantation into the human body for monitoring tissue electrical activity and for tissue electrical stimulation, the electrode comprising:
   (a) a flexible electrode body;
   (b) a connector portion having a plurality of connectors for connection to external monitoring equipment, said connector portion being unitary with said electrode body;
   (c) said electrode body and said connector portion having a thin, flexible, non-conducting backing material;
   (d) a printed circuit formed on said flexible backing material, said printed circuit further comprising a plurality of electrical contact areas of a flexible conductive material for contacting the tissue, and a plurality of electrical leads connecting said electrical contact areas to said connectors of said connector portion, each said electrical contact area having a height; and
   (e) a flexible, non-conducting covering material covering said printed circuit, said flexible covering material having a thickness less than said electrical contact area height, said electrical contact areas protruding through said covering material whereby said protruding contact areas provide a means to contact the tissue to be monitored and stimulated.

2. The implantable electrode of claim 1, wherein the electrode body is flat and elongated.

3. The implantable electrode of claim 1, wherein the flexible, non-conducting backing material further comprises mylar.

4. The implantable electrode of claim 1, wherein the flexible, non-conducting backing material further comprises silicone.

5. The implantable electrode of claim 1, wherein the electrical contact areas further comprise a metal.

6. The implantable electrode of claim 5, wherein the metal is selected from the group consisting of stainless steel, platinum, and platinum/iridium.

7. The implantable electrode of claim 1, wherein the flexible, non-conducting covering material further comprises mylar.

8. The implantable electrode of claim 1, wherein the flexible, non-conducting covering material further comprises silicone.

9. A method of manufacturing an electrode for implantation into the human body for monitoring tissue electrical activity and for tissue electrical stimulation, comprising the steps of:
   (a) producing a flexible, elongated electrode body and a connector portion, said connector portion being connected to said electrode body, and both said electrode body and said connector portion being comprised of a thin, flexible, non-conducting backing material;
   (b) providing a printed circuit on said flexible, non-conducting backing material, said providing of said printed circuit further comprising providing a plurality of electrical contact areas of a conductive material for contacting the tissue, a plurality of connectors for connection to external monitoring equipment, and a plurality of electrical leads connecting the electrical contact areas to the connectors; and
   (c) covering the printed circuit with a flexible, non-conductive covering material having a thickness less than the height of said electrical contact areas whereby the electrical contact areas protrude through the covering material to provide a means to contact the tissue to be monitored.

10. The method of manufacturing of claim 9, wherein the electrode body produced is flat and elongated.

11. The method of manufacturing of claim 9, wherein the flexible, non-conducting backing material provided further comprises mylar.

12. The method of manufacturing of claim 9, wherein the flexible, non-conducting backing material provided further comprises silicone.

13. The method of manufacturing of claim 9, wherein the electrical contact areas provided further comprise a metal.

14. The method of manufacturing of claim 13, wherein the metal provided is selected from the group consisting of stainless steel, platinum, and platinum/iridium.

15. The method of manufacturing of claim 9, wherein the flexible, non-conducting covering material provided further comprises mylar.

16. The method of manufacturing of claim 9, wherein the flexible, non-conducting covering material provided further comprises silicone.

17. An implantable subdural electrode for monitoring tissue electrical activity and for tissue electrical stimulation, comprising:
   (a) a flexible electrode body comprised of a thin, flexible, non-conductive backing material, said electrode body having a connector portion comprised of a plurality of connectors for connection to external monitoring equipment;
   (b) a printed circuit on said flexible backing material, said printed circuit further comprising a plurality of electrical contact areas of a flexible conductive material for contacting the tissue, and a plurality of electrical leads connecting said electrical contact areas to said connectors of said connector portion, each said electrical contact area having a predetermined height; and
   (c) a flexible, non-conducting material covering said printed circuit, said flexible material having a thickness less than said electrical contact area height, said electrical contact areas protruding through said material whereby said protruding contact areas provide a means to contact the tissue to be monitored and stimulated.

18. The method of manufacturing of claim 9, wherein the printed circuit is provided by a means selected from the group consisting of etching and printing.

19. The subdural electrode of claim 17, wherein said electrical contact areas are comprised of a metal.

20. The subdural electrode of claim 19, wherein said metal is selected from the group consisting of stainless steel, platinum, and platinum/iridium.

21. The subdural electrode of claim 17, wherein said covering material and said backing material are comprised of a material selected from the group of materials consisting of silicone and mylar.

* * * * *